United States Patent

Sheley

(10) Patent No.: US 9,395,344 B2
(45) Date of Patent: Jul. 19, 2016

(54) GAS SENSOR WITH THERMAL MEASUREMENT COMPENSATION

(71) Applicant: Veris Industries, Inc., Tualatin, OR (US)

(72) Inventor: John Hanson Sheley, Portland, OR (US)

(73) Assignee: Veris Industries, LLC, Tualatin, OR (US)

( * ) Notice: Subject to any disclaimer, the term of this patent is extended or adjusted under 35 U.S.C. 154(b) by 247 days.

(21) Appl. No.: 14/156,236

(22) Filed: Jan. 15, 2014

(65) Prior Publication Data

US 2014/0216137 A1    Aug. 7, 2014

Related U.S. Application Data

(60) Provisional application No. 61/761,404, filed on Feb. 6, 2013.

(51) Int. Cl.
*G01N 7/00* (2006.01)
*G01N 9/00* (2006.01)
*G01N 25/00* (2006.01)
*G01N 29/02* (2006.01)
*G01N 33/00* (2006.01)

(52) U.S. Cl.
CPC .......... *G01N 33/0016* (2013.01); *G01N 33/004* (2013.01)

(58) Field of Classification Search
None
See application file for complete search history.

(56) References Cited

U.S. PATENT DOCUMENTS

| | | | |
|---|---|---|---|
| 3,911,386 A | 10/1975 | Beaudoin et al. | |
| 3,933,028 A | 1/1976 | Laud et al. | |
| 3,959,765 A | 5/1976 | Stewart | |
| 4,147,513 A | 4/1979 | Bienkowski et al. | |
| 4,164,699 A | 8/1979 | Timoshenko et al. | |
| 4,193,965 A | 3/1980 | Cullingford et al. | |
| 4,214,472 A | 7/1980 | Maxwell et al. | |
| 4,223,293 A | 9/1980 | Springer et al. | |
| 4,225,842 A | 9/1980 | Schlesselman et al. | |
| 4,236,138 A | 11/1980 | Segawa et al. | |
| 4,288,774 A | 9/1981 | Takami et al. | |
| 4,294,801 A | 10/1981 | Segawa et al. | |
| 4,309,897 A | 1/1982 | Springer et al. | |
| 4,333,067 A | 6/1982 | Kugimiya et al. | |
| 4,414,531 A | 11/1983 | Novak | |
| 4,583,070 A | 4/1986 | Okayama | |
| 4,703,646 A * | 11/1987 | Muller | G01N 27/4141 338/34 |
| 5,889,196 A * | 3/1999 | Ueno | G01N 27/407 204/429 |
| 5,922,939 A | 7/1999 | Cota | |
| 6,235,243 B1 * | 5/2001 | Fleischer | G01N 27/12 422/94 |
| 6,453,723 B1 * | 9/2002 | Ichikawa | G01N 33/0011 422/98 |
| 6,719,950 B2 | 4/2004 | Day et al. | |
| 6,736,001 B1 * | 5/2004 | Mueller | G01N 27/12 422/94 |
| 6,843,105 B1 | 1/2005 | France | |
| 7,387,811 B2 | 6/2008 | Selvamanickam | |
| 7,404,883 B2 | 7/2008 | Hahn et al. | |
| 7,469,586 B2 | 12/2008 | Wild et al. | |

(Continued)

*Primary Examiner* — Peter Macchiarolo
*Assistant Examiner* — Jermaine Jenkins
(74) *Attorney, Agent, or Firm* — Chernoff Vilhauer McClung & Stenzel, LLP

(57) ABSTRACT

A gas sensing device that includes differential temperature compensation.

14 Claims, 3 Drawing Sheets

(56) References Cited

U.S. PATENT DOCUMENTS

| | | |
|---|---|---|
| 7,855,655 B2 | 12/2010 | Hunter et al. |
| 7,902,992 B2 | 3/2011 | Hunter |
| 7,910,155 B2 | 3/2011 | Lee et al. |
| 8,212,548 B2 | 7/2012 | Parker et al. |
| 8,268,386 B2 | 9/2012 | Selvamanickam et al. |
| 8,421,443 B2 | 4/2013 | Bitsch et al. |
| 8,421,639 B2 | 4/2013 | Bitsch et al. |
| 8,972,204 B2 * | 3/2015 | Kellaway ............ G01N 27/123 702/24 |
| 9,027,387 B2 * | 5/2015 | Blackburn ......... G01N 27/4067 324/71.5 |
| 9,068,924 B2 * | 6/2015 | Biskupski .......... G01N 27/4075 |

* cited by examiner

GAS SENSOR WITH THERMAL MEASUREMENT COMPENSATION

CROSS-REFERENCE TO RELATED APPLICATIONS

This application claims the benefit of U.S. Provisional App. No. 61/761,404, filed Feb. 6, 2013.

BACKGROUND OF THE INVENTION

The present invention relates generally to a gas sensor with thermal measurement compensation.

A gas detector is a device which detects the presence of a gas within an area, often as part of a safety system. Upon detecting a gas leak the system may be used to interface with a control system so that appropriate action may be taken, such as shutting down the gas leak or otherwise sounding an alarm.

Gas detectors typically measure the concentration of a particular gas using a sensing device, such as a gas sensing module. The gas sensing module provides an output to a microcontroller, which typically sends an alarm signal to a control system if the gas level exceeds some threshold level. Many gas detectors have narrow limits on the specified accuracy, such as within a range of 2% accuracy, which is difficult to maintain in many operating environments especially with temperature variations.

What is desired therefore is a power meter with gas sensor with thermal measurement compensation.

The foregoing and other objectives, features, and advantages of the invention may be more readily understood upon consideration of the following detailed description of the invention, taken in conjunction with the accompanying drawings.

DETAILED DESCRIPTION OF PREFERRED EMBODIMENT

Figure 1:
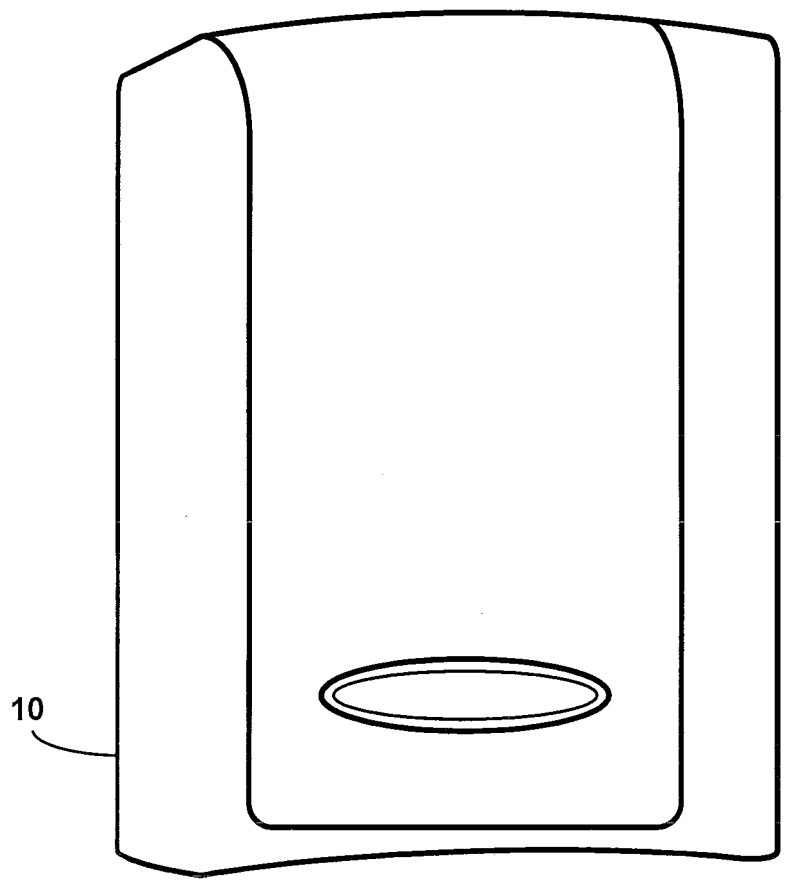
FIG. 1 illustrates a housing for a gas sensor.
Figure 2:
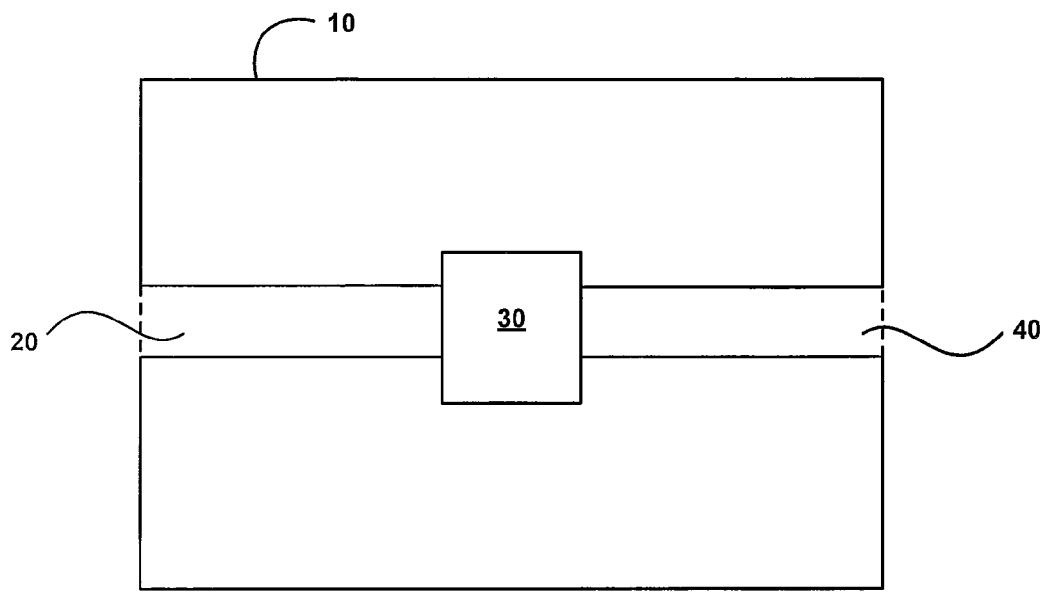
FIG. 2 illustrates a housing and gas sensing device.

Referring to FIG. 1, a gas detecting device for the measurement of gases in an environment is positioned within a housing 10. Referring also to FIG. 2, the gas housing includes an air intake passage 20 that directs gas to a gas sensing device 30. The gas sensing device 30 may be a electrochemical device or any other suitable device to sense gas levels of a particular gas, such as for example $CO_2$. The gas passing through or otherwise in communication with the gas sensing device 30 passes through the air outtake passage 40 that directs gas out of the housing 10.

Figure 3:
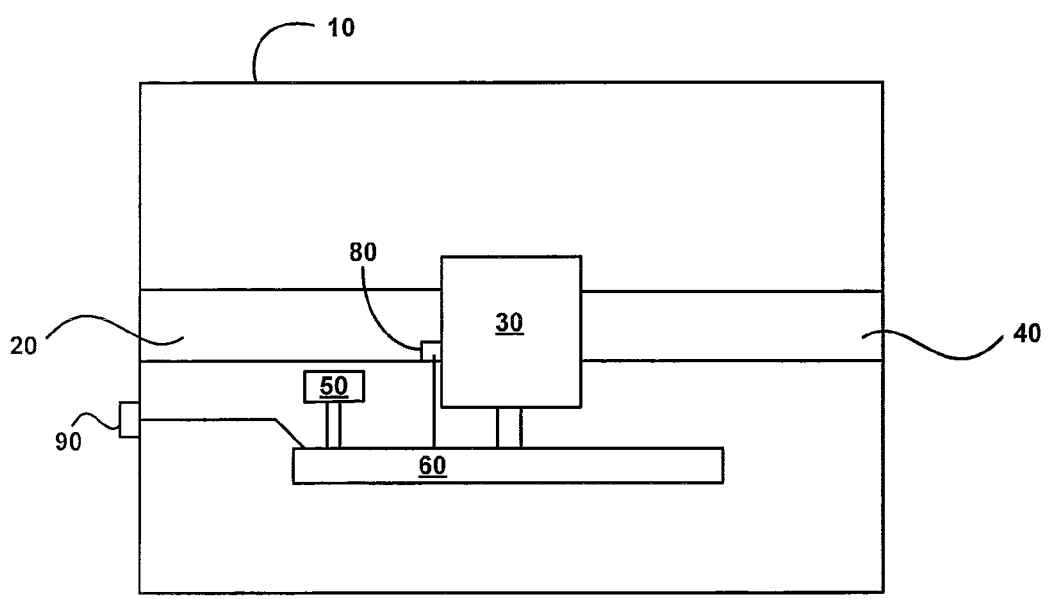
FIG. 3 illustrates a housing, gas sensing device, and temperature sensors.
Figure 4:
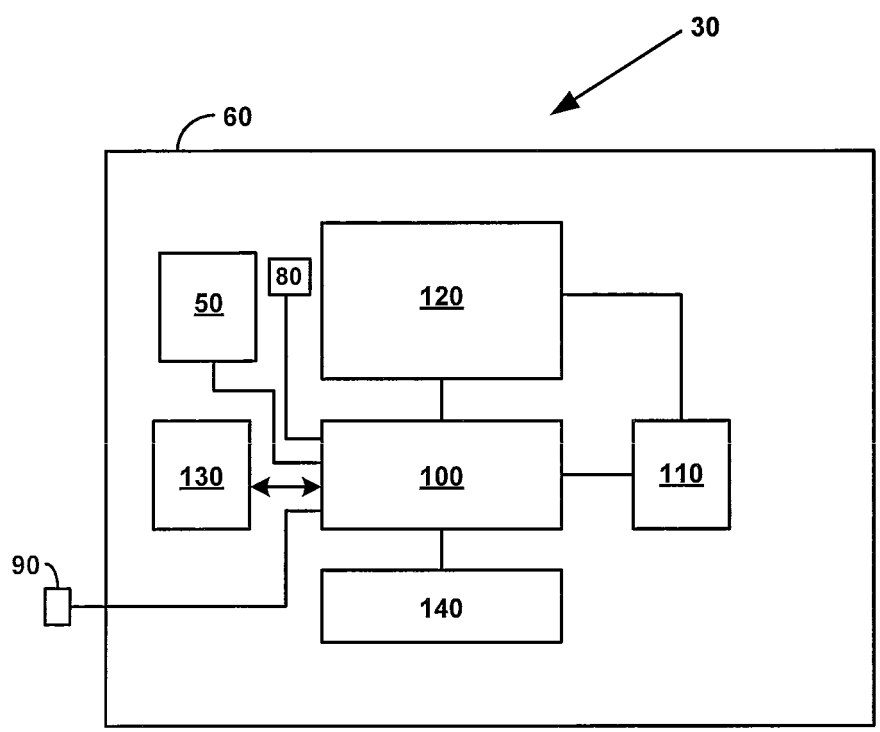
FIG. 4 illustrates a circuit board for the housing including the gas sensor.

Referring to FIG. 3, in many environments it is desirable to measure the gas at a relatively consistent temperature, therefore one or more heated components 50 may be in thermal communication with the gas passing through the air intake passage 20 and supported by a circuit board 60. Referring also to FIG. 4, the circuit board 60 may also support a gas sensor 120, a microcontroller 100, a battery (or other power source) 110, a memory 130, input/output communications 140, and other components. Each of the components supported by the circuit board 60 may be in communication with one another, typically receiving and/or providing communication to and from the microcontroller 100. The heated components 50 may be components specifically selected to heat up the gas in the air intake passage 20, or otherwise the gas sensing device may use components supported by the circuit board 60 which tend to heat up the gas in the air intake passage 20. The heated components 50 may be actively heated by signaling from the microcontroller 100. Preferably, the heated components 50 may be actively heated to a desired temperature by the microcontroller 100.

The heat provided to the gas in the air intake passage 20 expands the gas sensed by the gas sensing device 30 and thereby distorts its measurement. The gas sensing device 30 may have a distortion of less than approximately 0%-1% over a 0 to 30 degrees Celsius operating range. However, with the addition of an active heating element so that gas within the air intake passage 20 is maintained in a range more suitable for the gas sensing device 30, such as for example generally +12 degrees Celsius, the accuracy may be compromised. For example, by including an active heating element 50 that maintains an internal environment of generally +12 degrees Celsius together with an external environment that is generally at −29 degrees Celsius, a measurement distortion of approximately 13.8% will likely result from the gas sensing device 30. When a preferred specification of a gas detecting device has a distortion of less than approximately 2%, a measurement distortion of approximately 13.8% is about 700% to large.

The second law of thermodynamics states that the entropy of an isolated system never decreases because isolated systems spontaneously evolve towards thermodynamic equilibrium—the state of maximum entropy. Accordingly, all real electronic devices generate heat which forces the gas to expand. The gas expansion effectively decreases the measured gas concentration by the gas sensing device 30. To estimate the amount of gas expansion a temperature sensor 80 may be in thermal communication with the gas within the air intake passage 30. Preferably, the internal temperature sensor 80 is located in a position adjacent to the gas sensing device 30 so that a more accurate temperature of the gas sensed by the gas sensing device 30 may be determined. The internal temperature sensor 80 is electrically connected to the microcontroller. The addition of the temperate sensor 80 together with a calibration of the gas sensing device 30 using calibration data stored together with the microcontroller, permits some calibration of the gas sensing device 30 with respect to the gas temperature.

For substantial temperature changes between the exterior temperature of the device and the interior temperature of the device as a result of the heating elements 50, the gas has substantial expansion that is not readily correctable as a result of calibration data associated with only the internal temperature sensor 80. To permit calibration of the gas expansion an external temperature sensor 90 is positioned such that it senses the temperature external to the housing. Preferably, the external temperature sensor 90 is affixed to the exterior surface of the housing 10, or otherwise suitable to sense the temperature of the exterior region of the periphery of the housing 10. With the combination of the external temperature sensor 90 and the internal temperature sensor 80, the microcontroller can determine the differential temperature change between the outside and the inside of the housing 10. Based upon the differential temperature, the microcontroller may determine the approximate change in the gas pressure within the housing 10.

The microcontroller may determine a molar concentration of the gas within the housing and thus with suitable modifications based upon the differential temperature, the molar concentration of the gas outside of the housing may be determined. The gas concentration may be represented by $PV=nRT$, where P is the pressure of the gas, V is the volumne of the gas, n is the amount of substance of gas (also known as the number of moles), T is the temperature of the gas, and R is the universal gas constant equal to the product of the Boltzmann constant and Avogradro constant. In SI units, P is measured in pascals, V is measured in cubic meters, n is measured in moles, and T in kelvin. R has the value of 8.314 $j*K^{-1}*mol^{-1}$ or 0.08206 $L*atm*mol^{-1}*k^{-1}$ if using pressure in standard atmospheres instead of pascals and volume in liters instead of cubic meters. This may be rearranged to $P/(R*T)=n/V=$molar concentration. For two different gas states e and s, where e is the exterior gas state and s is the interior gas state, it may be referenced as follows. $Pe/(R*Te)=n/Ve=$molar concentration e, and, $Ps/(R*Ts)=n/Vs=$molar concentration s. Combining the relationships for s and e, simplified for the internal and external pressure being essentially the same, may be referenced as follows. molar concentration e=(molar concentration s*Ts)/Te. In this manner, the adjusted external gas concentration may be calculated by the microcontroller based upon the differential temperatures. The adjusted external gas concentration may be provided to a display, transmitted to another device using any suitable signal such as for example a 4-20 ma signal, a digital signal, an alarm signal, an analog signal, a Modbus protocol based signal, an $I^2C$ protocol based signal, etc.

In some cases, the temperature sensor 80 is not sufficiently accurate to permit adjustment of the molar concentration of the sensing device 120. For those situations it is desirable to include the temperature sensor 80 within the housing that encapsulates the sensing device 120 which increases the accuracy of the system.

In some cases, it is desirable to include a single air intake passage 20 that is interconnected to a pair of different gas sensors, together with a single internal temperature sensor 80 and external temperature sensor 90. In addition, different differential temperature calibration may be used for each of the different gas sensors, each suitable for the particular gas sensor. In this manner, a more efficient gas detection system is provided.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

I claim:

1. A gas detector including a housing comprising:
   (a) said housing enclosing a gas sensing device that provides an estimate of an amount of a gas expansion;
   (b) said housing including an input for gas to reach said gas sensing device within said housing;
   (c) said housing including an output for gas to exit said gas sensing device after being sensed by said gas sensing device;
   (d) said housing enclosing a heating element in thermal communication with gas within said input;
   (e) an internal temperature sensor enclosed within said housing;
   (f) said housing including a modification circuit that modifies said estimate of said gas based upon a differential temperature between an external signal received by said modification circuit from an exterior temperature sensor of an exterior temperature of said housing and an internal signal received by said modification circuit from said internal temperature sensor of an interior temperature of said housing.

2. The gas detector of claim 1 wherein said gas sensing device senses carbon dioxide.

3. The gas detector of claim 1 further comprising a heating element that selectively increases the temperature within said housing.

4. The gas detector of claim 3 wherein said heating element is controlled by a microcontroller.

5. The gas detector of claim 4 wherein said heating element is heated to a predetermined temperature by said microcontroller.

6. The gas detector of claim 5 wherein said predetermined temperature is monitored by a temperature sensor enclosed within said housing.

7. The gas detector of claim 1 wherein said gas sensing device is an electrochemical device.

8. The gas detector of claim 1 wherein said gas sensing device senses gas at a relatively constant temperature to provide said estimate.

9. The gas detector of claim 1 wherein said gas sensing device senses gas at a relatively constant temperature to provide said estimate.

10. The gas detector of claim 1 wherein said external temperature sensor is affixed to an exterior surface of said housing.

11. The gas detector of claim 1 wherein said gas sensing device determines a molar concentration of said gas.

12. The gas detector of claim 1 wherein said gas sensing device and said internal temperature sensor are encapsulated together.

13. The gas detector of claim 12 wherein said gas sensing device and said second gas sensing device each estimate said gas based upon said differential temperature.

14. The gas detector of claim 1 further comprising a second gas sensing device.

* * * * *